United States Patent [19]
Capella et al.

[11] Patent Number: 5,891,083
[45] Date of Patent: Apr. 6, 1999

[54] SUCTION LIPOLYSIS

[76] Inventors: Rafael F. Capella, Laual Rd., Tuxedo Park, N.Y. 10987; Joseph F. Capella, 1230 Park Ave., New York, N.Y. 10128

[21] Appl. No.: 837,709

[22] Filed: Apr. 22, 1997

[51] Int. Cl.[6] ...................................................... A61M 1/00
[52] U.S. Cl. .............................. 604/28; 604/56; 604/113; 435/267
[58] Field of Search .................................. 604/28, 35, 49, 604/56, 22, 118, 113–114, 902; 435/267

[56] References Cited

U.S. PATENT DOCUMENTS

| | | |
|---|---|---|
| 3,634,191 | 1/1972 | Laboureur . |
| 4,968,621 | 11/1990 | Pfleiderer et al. . |
| 5,089,414 | 2/1992 | Christner et al. . |
| 5,143,063 | 9/1992 | Fellner . |
| 5,422,261 | 6/1995 | Lee et al. . |
| 5,424,208 | 6/1995 | Lee et al. . |

*Primary Examiner*—Mark Bockelman
*Attorney, Agent, or Firm*—McGlew and Tuttle

[57] ABSTRACT

A compound, solution of carrier and the compound and a medical procedure is provided for suction lipolysis. The compound is preferably either one or more enzymes and/or emulsifying agents and/or detergents which digest or dissolve fat in the subcutaneous tissues. Both enzymes which degrade fats and emulsifying agents can be used according to the invention. The carrier is preferably a saline solution. A suction lipolysis procedure is provided including the steps of providing a biological and/or chemical compound which digests or dissolves fat in the subcutaneous tissues. The compound is dissolved into a saline solution and/or is suspended in a saline solution. The combination compound and saline solution is then heated to the body temperature (temperature of the patient or subject). The compound and saline solution including the compound is then injected into the subcutaneous tissue. Liposuction is then performed (suction lipectomy). The step of performing liposuction is preferably initiated after a period of time has elapsed after the saline solution and compound are infiltrated into the subcutaneous tissue.

6 Claims, No Drawings

SUCTION LIPOLYSIS

FIELD OF THE INVENTION

The invention relates generally to liposuction or suction lipectomy and more particularly to a compound, a solution containing the compound and to an improved procedure for removal of subcutaneous fat within humans using a mechanical suction device.

BACKGROUND OF THE INVENTION

Liposuction or suction lipectomy is a procedure that is performed worldwide and is currently the most commonly done aesthetic operation in the United States. This technique involves the removal of subcutaneous fat with a mechanical suction device or hand held syringe.

To assist in the removal of fat, produce hemostasis and reduce swelling, solutions are injected into the subcutaneous tissues prior to initiating suction lipectomy. The solutions are mostly saline into which varying amounts of lidocaine, epinephrine and steroids have been added. Testicular bovine protein enzymes have been used to promote diffusion of the solution in some cases. After the fat cells (adiposities) are mechanically broken by the suction devices, the fat particles are removed. Other less frequently performed procedures utilize electric heat or ultrasound to breakup the fat.

SUMMARY AND OBJECTS OF THE INVENTION

It is an object of the invention to provide a compound which degrades fats and a solution containing the compound which effectively dissolves subcutaneous fat when injected into the subcutaneous tissue in a suction lipolysis procedure, prior to the step of suctioning and (lipolysis).

It is a further object of the invention to provide a procedure using one or more compounds which breakdown fat into the saline solution which is injected into the patient.

According to the invention, a procedure referred to herein as suction lipolysis is provided which significantly facilitates and expedites a liposuction type procedure.

According to a first aspect of the invention, a compound is provided for use in a suction lipolysis procedure as defined herein. The compound is preferably either an enzyme and/or an enzyme suspended or dissolved in a saline solution, particularly lipase and/or colipase.

Enzymes such as lipase and colipase are produced by the pancreas and have been shown to be enzymes which degrade fats. The compound according to the invention could also be an emulsifying agent which facilitates digestion. Further, detergents may also be used. Emulsifying agents such as bile salts, including cholic acid, are produced by the liver. Both groups, namely enzymes which degrade fats and emulsifying agents can be used according to the invention as these have been shown to work invetro and have been extensively studied with the aim of lowering cholesterol (a form of fat) in the blood.

According to another aspect of the invention, a suction lipolysis procedure is provided including the steps of providing a compound selected from the group consisting of enzymes which degrade fats and emulsifying agents. More preferably, lipase is employed. The compound which consists of one or more of enzymes that degrade fats and/or emulsifying agents is dissolved into a saline solution and/or is suspended in a saline solution. The combination compound and saline solution is then heated to the body temperature (temperature of the patient or subject). The compound and saline solution including the compound is then injected into the subcutaneous tissue. Liposuction is then performed (suction lipectomy). The step of performing liposuction is preferably initiated after a period of time has elapsed after the saline solution and compound are infiltrated into the subcutaneous tissue.

The various features of novelty which characterize the invention are pointed out with particularity in the claims annexed to and forming a part of this disclosure. For a better understanding of the invention, its advantages and specific objects attained by its uses, reference is made to the examples and descriptive matter in which preferred embodiments of the invention are illustrated.

DESCRIPTION OF THE PREFERRED EMBODIMENTS

The invention provides a compound for a particular use, a solution including the dissolved compound and a carrier such as saline solution or the compound suspended in the carrier. The invention also provides a as well for suction lipolysis.

Mammals, including humans, use enzymes to degrade fats, and emulsifying agents to facilitate digestion. These enzymes, lipase and colipase are produced by the pancreas. The emulsifying agents such as bile salts are produced by the liver. Both groups of compounds, namely enzymes to degrade fats, and emulsifying agents to facilitate digestion have been shown to work in vitro and have been extensively studied with the aim of lowering cholesterol (a form of fat) in the blood. These substances have never been used to dissolve subcutaneous fat in vitro or in living organisms. Enzymes to degrade fats, and emulsifying agents to facilitate digestion are used according to the invention to dissolve subcutaneous fat in vitro. Detergents are also used.

Of enzymes which degrade fats, and emulsifying agents which facilitate digestion lipase, colipase and bile salts are preferred according to the invention.

PREPARATION OF SOLUTION

According to a further aspect of the invention, a solution is provided which is useful for a suction lipolysis procedure. The solution is prepared by using one of the compounds described above, dissolved in and/or suspended in saline solution. A preferred solution according to the invention provides 500 cc's of saline solution to each several grams or sever cc's of the compound.

SUCTION LIPOLYSIS SOLUTION EXAMPLE 1

To 500 cc's of saline solution 2 g. of lipase is mixed until the lipase is completely dissolved in the saline solution to provide the suction lipolysis solution of the invention. The amount of lipase can also be varied for example from about 0.2 g to 10 g. If an amount of the compound is used which is in the upper range, for example 10 g or higher, the compound may be suspended in the saline solution (if it will not fully dissolve). The solution may also include varying amounts of lidocaine, epinephrine and steroids or even testicular bovine protein enzymes to promote diffusion of the solution.

SUCTION LIPOLYSIS SOLUTION EXAMPLE 2

To 500 cc's of saline solution 2 g. of colipase is mixed until the colipase is completely dissolved in the saline solution to provide the suction lipolysis solution of the invention. The amount of colipase can also be varied for example from about 0.2 g to 10 g. If an amount of the compound is used which is in the upper range, for example 10 g or higher, the compound may be suspended in the saline solution (if it will not fully dissolve). The solution may also include varying amounts of lidocaine, epinephrine and steroids or even testicular bovine protein enzymes to promote diffusion of the solution.

SUCTION LIPOLYSIS SOLUTION EXAMPLE 3

To 500 cc's of saline solution 1 cc of cholic acid is mixed to provide the suction lipolysis solution of the invention. The amount of cholic acid can also be varied for example from about 0.01 cc to 10 cc per 500 cc's of saline solution. The solution may also include varying amounts of lidocaine, epinephrine and steroids or even testicular bovine protein enzymes to promote diffusion of the solution.

SUCTION LIPOLYSIS SOLUTION EXAMPLE 4

To 500 cc's of saline solution 1 g. of lipase and 1 g. of colipase are mixed until the lipase and colipase are completely dissolved in the saline solution to provide the suction lipolysis solution of the invention. The amount of lipase and colipase can also be varied for example from about 0.1 g to 5 g. The ratio of lipase to colipase (or vice versa) can be varied from the 50-50 ratio. If an amount of the compounds is used which is in the upper range, for example 10 g or higher, the compound may be suspended in the saline solution (if it will not fully dissolve). The solution may also include varying amounts of lidocaine, epinephrine and steroids or even testicular bovine protein enzymes to promote diffusion of the solution.

SUCTION LIPOLYSIS SOLUTION EXAMPLE 5

To 500 cc's of saline solution 1.5 g. of lipase and 0.5 g. of colipase are mixed until the lipase and colipase are completely dissolved in the saline solution. Additionally an amount of bile salts or cholic acid and or other emulsifying agents is added (such as 1 cc of cholic acid) to provide the suction lipolysis solution of the invention. The amount of lipase and colipase can also be varied for example from about 0.1 g to 5 g. The ratio of lipase to colipase (or vice versa) can be varied. However, using colipase in a smaller quantity (lower ratio of colipase to lipase) appears to be effective. It appears that colipase acts as a coenzyme and it has been shown that this greatly increases the activity of the lipase. If an amount of the compounds is used which is in the upper range, for example 10 g or higher, the compound may be suspended in the saline solution (if it will not fully dissolve). The solution may also include varying amounts of lidocaine, epinephrine and steroids or even testicular bovine protein enzymes to promote diffusion of the solution.

SUCTION LIPOLYSIS PROCEDURE

A suction lipolysis procedure is provided according to the invention using the compound of the invention. More preferably, the compound is included in a carrier such as a saline solution to provide the suction lipolysis solution of the invention.

The suction lipolysis solution of the invention is heated to the body temperature (temperature of the patient or subject). The suction lipolysis solution of the invention, namely the compound and saline solution (and possibly other compounds as required) is then injected into the subcutaneous tissue. Liposuction is then performed (suction lipectomy). The step of performing liposuction is preferably initiated after a period of time has elapsed after the saline solution and compound are infiltrated into the subcutaneous tissue.

PROCEDURE EXAMPLE

A large portion of skin and fat removed 24 hours previously from a patient by a surgical procedure called panniculectomy. The specimen was divided into two halves, each measuring about 30×40 cms. On one side, the control, the standard procedure was carried out, infiltrating the area with 500 cc of normal saline solution prior to liposuction. On the experimental side, the same amount of saline solution was injected, but in this case several grams of enzyme lipase had been added in a dissolved form. The saline solution was heated to near body temperature for both portion of the experiment. Fifteen minutes after each side was infiltrated, syringe liposuction was performed on each side for 20 minutes. The procedure may also involve the use of cannulas and the application of negative pressure.

A marked difference was found in the amount and characteristics of the fluid extracted from the two halves of subcutaneous tissue. In the side used as a control, about 300 cc of a two layered fluid was extracted. The lower or more dense layer had the appearance of water (saline) slightly tinged with blood. The upper or more dense layer was composed of globules of intact fat, measuring approximately 0.2 to 0.4 cm. This layer was a pale yellow.

In the portion of the experiment using the suction lipolysis solution (the lipase experiment), the extracted fluid measured about 400 cc. It contained three layers. The lower layer was tinged with blood, but it appeared essentially saline. The second larger layer again made up of globules of fat, but of slightly smaller diameter, approximately 0.2 cm. The least dense layer had an oily appearance. The addition of the lower and upper layers was proportionally bigger than the lower layer of the experimental portion used as the control.

The experimental findings were remarkable in that there was significantly more extracted fluid, and that a third layer of oil was additionally present. The control side contained a minimal amount of free oil.

It was concluded from this experiment that the lipase decreased the size of fat globules, and degraded some the fat to the breakdown products glycerol and fatty acids.

This initial experiment was carried out in a crude fashion. In future experiments, the lipase could work much more effectively by careful control of enzyme concentration, temperature, PH and contact time. In addition, a coenzyme of lipase could be added, colipase. It has been shown to greatly increase the activity of lipase. The action of bile salts and other emulsifying agents may also be beneficial in combination or as the primary or exclusive active compound added to the carrier.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

What is claimed is:

1. A suction lipolysis procedure comprising the steps of:

providing one or a combination of chemical and biological compounds to digest or dissolve fat in the subcutaneous tissues of a patient;

mixing the compound or compounds with a carrier;

injecting the mixed compound and carrier into the subcutaneous tissue of a subject; and performing liposuction.

2. The suction lipolysis procedure of claim 1, wherein said step of providing one or a combination of chemical and biological compounds to digest or dissolve fat in the subcutaneous tissues includes providing a compound selected from the group consisting of one or more enzymes which degrade fats and/or one or more emulsifying agents and/or one or more detergents.

3. The suction lipolysis procedure of claim 2, wherein the one or more enzymes are selected from the group consisting of lipase and colipase.

4. The suction lipolysis procedure of claim 2, wherein a bile salt is the one or more emulsifying agents.

5. The suction lipolysis procedure of claim 1, wherein said one or a combination of chemical and biological compounds to digest or dissolve fat in the subcutaneous tissues consists essentially of one or more of lipase, colipase and bile salts and said carrier comprises a saline solution.

6. The suction lipolysis procedure of claim 1, wherein the mixed compound and carrier is heated to the temperature of the subject prior to being injected and the step of performing liposuction is preferably initiated after a period of time has elapsed after the carrier and compound are infiltrated into the subcutaneous tissue.

* * * * *